(12) United States Patent
Taipale et al.

(10) Patent No.: US 6,526,154 B1
(45) Date of Patent: Feb. 25, 2003

(54) METHOD AND APPARATUS FOR DETERMINING THE PORTION OF WOOD MATERIAL PRESENT IN A STREAM OF BARK

(75) Inventors: Esa Taipale, Lahti (FI); Rudolf Mayböck, St. Bartholomä (AT)

(73) Assignee: Andritz-Patentverwaltungs-GmbH, Graz (AT)

(*) Notice: Subject to any disclaimer, the term of this patent is extended or adjusted under 35 U.S.C. 154(b) by 0 days.

(21) Appl. No.: 09/424,326
(22) PCT Filed: May 19, 1998
(86) PCT No.: PCT/FI98/00420
§ 371 (c)(1), (2), (4) Date: Jan. 12, 2000
(87) PCT Pub. No.: WO98/53313
PCT Pub. Date: Nov. 26, 1998

(30) Foreign Application Priority Data

May 19, 1997 (FI) .................................................. 972123

(51) Int. Cl.[7] .............................................. G06K 9/00
(52) U.S. Cl. ...................................... 382/100; 382/108
(58) Field of Search ................................. 382/100, 108

(56) References Cited

U.S. PATENT DOCUMENTS

| | | | |
|---|---|---|---|
| 4,266,675 A | 5/1981 | Barwise et al. | 209/540 |
| 4,691,231 A * | 9/1987 | Fitzmorris et al. | 209/522 |
| 5,274,244 A | 12/1993 | Johansson et al. | 250/559.05 |
| 5,544,757 A | 8/1996 | Geiger et al. | 209/518 |
| 5,757,977 A * | 5/1998 | Mancuso et al. | 358/447 |
| 6,175,092 B1 * | 1/2001 | Binette et al. | 209/587 |

FOREIGN PATENT DOCUMENTS

| | | |
|---|---|---|
| EP | 0 831 320 A2 | 3/1998 |
| FI | 90918 | 12/1993 |

OTHER PUBLICATIONS

"Image Enhancement with a Fuzzy Logic Approach" by J. Hsieh. Electronic Letters, vol.:31, Issue: 9, Apr. 27, 1995, pp. 708–710.*

* cited by examiner

Primary Examiner—Leo Boudreau
Assistant Examiner—Hussein Akhavannik
(74) Attorney, Agent, or Firm—Alix, Yale & Ristas, LLP

(57) ABSTRACT

A method and an apparatus which defines the amount of wood material present in a bark flow and controls a debarking process on the basis of the data to reduce wood losses in the debarking process. In accordance with the invention, the bark flow is imaged by a camera and an image processing unit processes the image by using different whitenesses of the picture elements or pixels of the image as a basis for defining programmatically the amount of wood material in the bark flow. The image processing unit is adapted to produce an output signal for controlling the debarking process. In addition, the invention also provides a method and an apparatus which defines the amount of wood material in a bark flow being moved to a combustion process and controls the combustion process on the basis of the data.

6 Claims, 2 Drawing Sheets

METHOD AND APPARATUS FOR DETERMINING THE PORTION OF WOOD MATERIAL PRESENT IN A STREAM OF BARK

CROSS-REFERENCE TO RELATED APPLICATION

This is the United States National Phase of International application Ser. No. PCT/FI98/00420 filed May 19, 1998.

BACKGROUND OF THE INVENTION

1. Field of the Invention

The present invention relates to a method and an apparatus for defining the portion of wood material present in a bark flow coming out from a debarking process and for controlling the barking process on the basis of said data for reducing wood losses in the debarking process.

2. Related Art

In debarking, usually a barking process carried out by means of a debarking drum, the object is to remove bark from the surface of trees so as to achieve a desired degree of debarking. At the same time, however, there occurs grinding off and crushing of wood material itself, said wood material representing wood loss as it becomes part of a bark flow. Naturally, it is desirable the wood loss is kept at a minimum, especially since wood is a major cost factor in the production of pulp and paper. Generally, the bark flow may contain wood on the order from 10% to about 40, which equals wood losses of about 20% to about 50% the total quantity of wood material used.

In the prior art, the portion or share of wood in a bark flow is measured by picking up a sample from the bark flow. The sample is handled manually to separate wood and bark material from each other, followed by drying and then measuring the relative amount of wood. Drying is necessary in order to compare dry weights. According to SCAN-standard, the drying takes 16 hours.

The above type measurements have been used mostly for statistics, yet such measurements have had little significance in terms of process control as the situation could have changed during the time period incurred during drying of the sample.

SUMMARY OF THE INVENTION

An object of the invention is to provide a method and an apparatus for measuring wood loss in a debarking process essentially in real time and, thus, to provide a for controlling the debarking process for reducing wood losses.

According to the invention, this object is achieved and a method of the invention is characterized in that a bark flow coming out from debarking is measured optically for its whiteness and the measuring result is used as a basis for determining programmatically by means of a data processing unit the amount of wood material in the bark flow, and that the debarking process is controlled on the basis of the amount of wood material determined from the bark flow.

It should be stressed that, in this application, the term whiteness refers not only to various grey levels but also to color separation.

The apparatus of the invention is characterized in that a bark flow coming out from debarking is adapted to be imaged by means of a camera, said image taken by the camera being adapted to be processed with an image processing unit which uses different whitenesses of the picture elements or pixels of the image as a basis for determining programmatically through multiple inerations portions of wood material in the bark flow, and that the image processing unit is adapted to produce an output signal for controlling the debarking process.

The image is preferably processed in image sections, the particular picture elements of which may be varied between iterations.

The real-time measuring of a bark flow in accordance with the invention for determining the amount of wood material contained in the bark flow offers in an average wood room a possibility of saving about 10% to 20% of the total amount of wood, which represents about 5,000to about 40,000 solid cubic meters of wood annually, depending on the size of a wood room.

In addition, the invention relates to a method and an apparatus for determining the portion of wood material present in a bark flow being delivered to a combustion process and for controlling the combustion process on the basis of said data for optimizing the combustion process.

Especially in power plants of sawmills, pulp and paper mills, which burn a mixture of bark and wood material, a problem is the fluctuation of a heat value of the mixture to be burned. The most important factor effecting to the heat value is the moisture of a mixture to be burned, but also the fluctuation of the relative portions of e.g. bark and wood material in a mixture to be burned has an effect on the heat value.

In the method of the invention, the effect of fluctuation between the relative portions of bark and wood material upon the heat value is resolved in such a manner that from a bark flow is measured optically its whiteness and the measuring result is used as a basis for determining programmatically by means of a data processing unit the amount of wood material in the bark flow, and that the amount of wood material determined from the bark flow is used as a basis for calculating a heat value for the material present in the bark flow and for controlling the burning process as necessitated by said value.

The apparatus of the invention is characterized in that a bark flow is adapted to be imaged by means of a camera, said image taken by the camera being adapted to be processed with an image processing unit which uses different whitenesses of the picture elements of the image as a basis for determining programmatically the portion of wood material in the bark flow, and that the image processing unit is adapted to produce an output signal for controlling the burning process.

BRIEF DESCRIPTION OF THE DRAWINGS

The invention will now be described in more detail with reference made to the accompanying drawing, in which:

In FIG. 1, reference numeral 1 designates a rotatable debarking drum, the trees to be barked being delivered therein through one end thereof by means of a infeed conveyor 2 and the debarked trees coming out of the other end on a discharge conveyor 3.

Figure 1:
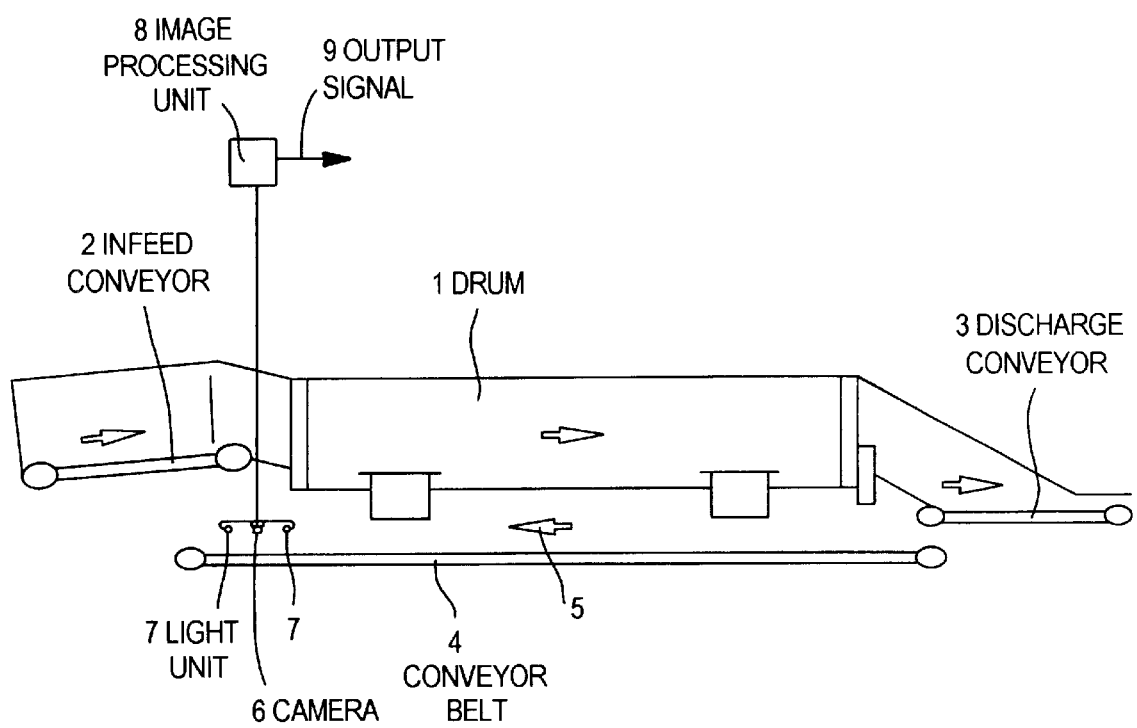
FIG. 1 shows schematically a wood room equipped with an apparatus according to one embodiment of the invention.

Rotation of the drum 1 causes rolling and hitting of the logs against each other, the bark being removed from the surface thereof and discharging from the drum 1 through bark slots (not shown) present in drum shell onto a conveyor belt 4 arranged below the drum 1. Depending on the process settings, however, the trees release at the same time more or less of the actual wood material, said wood material representing wood losses as it discharges through the bark slots along with barks.

In order to photograph a wood flow falling onto the conveyor belt 4 set below the drum 1 and moving thereon in the direction of an arrow 5, a camera 6 and necessary lighting units 7 have been mounted above the discharge end of the conveyor belt 4.

The camera 6 is connected to an image processing unit 8, which uses various whitenesses in the picture elements of an image taken by the camera 6 as a basis for determining programmatically the amount of wood material in the bark flow.

The image processing unit 8 is adapted to produce an output signal 9 for controlling the debarking process. Most preferably, the output signal 9 is adapted to automatically control the debarking process.

The measurement of a stream of bark is essentially performed as a realtime measurement and preferably by carrying out the measurement from a moving bark flow. Naturally, it is also possible to pick up samples and photograph those in a stationary position.

The image processing proceeds as follows.

1. The preset threshold values for whitenesses are used as a basis for mapping large pieces of wood from small pieces of bark and the background (conveyor belt).

For example, if the whiteness varies e.g. between 0 and 256, wherein, in terms of whiteness, zero represents black and 256 white, the preset threshold values, on the basis of experiments, are set for certain species of wood for example at 120 and 200, the whiteness 200–256 representing wood and 0–120 representing bark.

2. The whitenesses of picture elements identified as bark or wood are set at the minimum or maximum, i.e. bark at the value of 0 and wood at the value of 256.

3. The new image, composed at the preceding stage, is analyzed by a mean-value filter, which studies the entire image in small sections and calculates an average whiteness from each section. The average or mean value is used as a basis for determining an image section either as wood, bark or unidentified to wait for the next cycle. This sequence separates small wood pieces and large bark pieces.

If the average falls on a range determined as wood (200–256) or as bark (0–120), such ranges are presented as values bark =0 and wood =256.

Sequences 1–3 are repeated until all pixels are determined or until reaching a preset number of iterations.

The operation of this system is based on the fact that the areas determined either as bark or wood influence the averages obtained from the mean-value filter over the next iteration cycle, each cycle thus providing a more complete result.

Figure 2A:
FIG. 2a shows an original black-and-white image taken of a stream of bark.

FIG. 2a depicts an example of an original image taken of a bark flow.

Figure 2B:
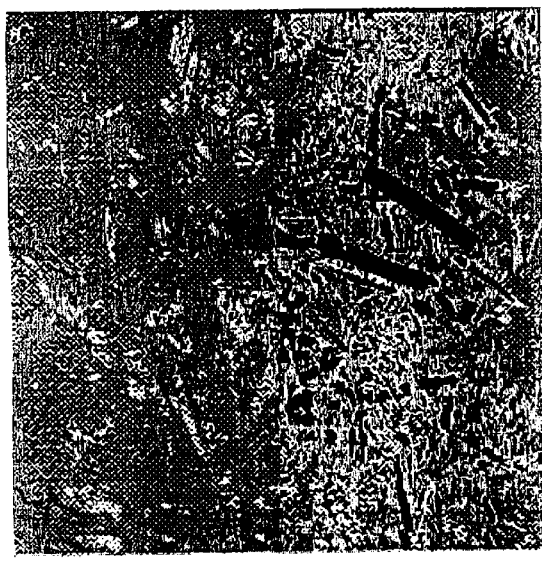
FIG. 2b shows shaping of the image of FIG. 2a after one iteration by the image processor.

FIG. 2b shows an original image corresponding to FIG. 2a and processed by means of the image processing unit 8, following the first iteration cycle. On the basis of whitenesses, it is possible to calculate in terms of the relative numbers of picture elements determined as wood, bark, or undefined that the amount of wood is 12%, the amount of bark 33, 1%, with more than a half, or 54.8%, consisting of an area still to be defined.

Figure 2C:
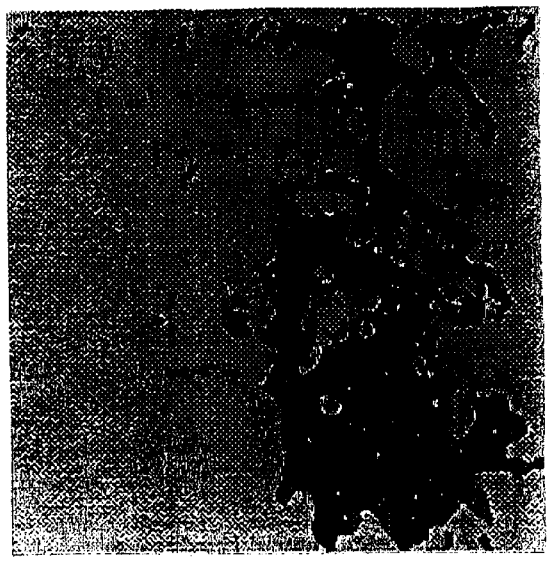
FIG. 2c shows shaping of the image of FIG. 2a after twenty iterations by the image processor.

In FIG. 2c, the original image (FIG. 2a) is illustrated in the same shape as FIG. 2b after the completion of 20 iteration cycles. On the basis of whitenesses, it is possible to calculate that the amount of wood is 27;4%, the amount of bark 70;5%, the amount of a still undefined area being no more than 2;1%. It will be understood that while FIG. 1 illustrates a method and, an apparatus for reducing wood losses in a debarking process, this is for illustrational purposes only. The basic concept of the invention can also be applied e.g. in such a way that any bark flow present on the conveyor belt 4 as shown in FIG. 1 and moving to be burned is analyzed as described in connection with FIG. 1, but what is calculated after determining the amount of wood material is the heat value of a material present in the bark flow and the combustion process is controlled on the basis thereof.

What is claimed is:

1. A method for defining the amount of wood material present in a bark flow coming out from a debarking process and for controlling the debarking process on the basis of said data for reducing wood losses in the debarking process, in which method the bark flow is measured optically for its whiteness and the measuring result is used as a basis for determining programmatically by means of a data processing unit the amount of wood material in the bark flow, and the debarking process being controlled on the basis of the amount of wood material determined from the bark flow, wherein an image taken of a bark flow is analyzed for whitenesses and the method for defining the amount of wood material comprises the steps of:

dividing the image into picture elements;

defining the whiteness of each picture element of the image in terms of at least a three-way split numerical scale, whose end points are m and n, one end point being applied to represent bark and the other to represent wood;

setting predetermined threshold values a and b wherein a<b, m<a<n, and b<n;

setting the value of a picture element to m, when the picture element has a whiteness within the range from m to a;

setting the value of a picture element to n, when the picture element has a whiteness within the range of from b to n;

maintaining the value of a picture element when the picture element has a whiteness within the range from a to b;

employing a mean value filter to process the image in image sections by means of a mean-value filter, each said image section consisting of a predetermined number of picture elements, the mean-value filter defining a whiteness mean value for each picture element of a particular image section and the obtained mean values are used as a basis for classifying all picture elements the particular image section with the same value m or n or with an unchanged value, if within the range from a to b;

repeating the foregoing steps until all picture elements are classified or until a predetermined number of iterations is achieved;

calculating the ratio of a number of picture elements representing wood to the total number of picture elements in an image for expressing the amount of wood present in the bark flow.

2. The method of claim 1 wherein the picture element comprises a pixel.

3. The method of claim 1 wherein the particular picture elements of which make up the image sections are varied from iteration to iteration.

4. A method for defining the amount of wood material in a bark flow being infed to a combustion process and for controlling and optimizing the combustion process on the basis of said data, in which method bark flow is measured optically for its whiteness and the measuring result is used as a basis for defining programmatically by a data processing unit the amount of wood material in the bark flow, and the amount of wood material defined from the bark flow is used as a basis for calculating a heat value for the material in the bark flow and for controlling the combustion process as necessitated by said heat value, wherein an image taken of a bark flow is analyzed for whitenesses and the method for defining the amount of wood material comprises the steps of;

dividing the image into picture elements;

defining the whiteness of each picture element of the image in terms of at least a three-way split numerical scale, whose end points are m and n, one end point being applied to represent bark and the other to represent wood;

setting predetermined threshold values a and b wherein a<b, m<a<n. and b<n;

setting the value of a picture element to m, when the picture element has a whiteness within the range from m to a;

setting the value of a picture element to n, when the picture element has a whiteness within the range of from b to n;

maintaining the value of a picture element when the picture element has a whiteness within the range from a to b;

employing a mean value filter to process the image in image sections, each said image section consisting of a predetermined number of picture elements, the mean-value filter defining a whiteness mean value for each picture element of a particular image section and the obtained mean values are used as a basis for classifying all picture elements of the particular image section with the same value m or n or with an unchanged value, if within the range from a to b;

repeating the foregoing steps until all picture elements are classified or until a predetermined number of iterations is achieved;

calculating the ratio of a number of picture elements representing wood to the total number of picture elements in an image for expressing the amount of wood present in the bark flow.

5. The method of claim 4 wherein the picture element comprises a pixel.

6. The method of claim 4 wherein the particular picture elements which make up the image section are varied from iteration to iteration.

* * * * *

UNITED STATES PATENT AND TRADEMARK OFFICE
CERTIFICATE OF CORRECTION

PATENT NO.    : 6,526,154 B1
DATED         : February 25, 2003
INVENTOR(S)   : Taipale et al.

It is certified that error appears in the above-identified patent and that said Letters Patent is hereby corrected as shown below:

Column 4,
Line 26, after "by" delete "means of".
Line 52, after "sections" delete "by means of a mean-value filter".

Column 5,
Line 19, after "of" delete ";" and insert -- : --.
Line 27, after "m<a<n" delete "." and insert -- , --.

Signed and Sealed this

Twenty-ninth Day of June, 2004

JON W. DUDAS
*Acting Director of the United States Patent and Trademark Office*